(12) United States Patent
Wang et al.

(10) Patent No.: US 7,304,735 B2
(45) Date of Patent: Dec. 4, 2007

(54) BROADBAND WAVELENGTH SELECTIVE FILTER

(75) Inventors: David Y. Wang, Fremont, CA (US); James L. Hendrix, Livermore, CA (US); Adam E. Norton, Palo Alto, CA (US)

(73) Assignee: KLA-Tencor Technologies, Milpitas, CA (US)

( * ) Notice: Subject to any disclaimer, the term of this patent is extended or adjusted under 35 U.S.C. 154(b) by 233 days.

(21) Appl. No.: 11/096,448

(22) Filed: Apr. 1, 2005

(65) Prior Publication Data

US 2005/0270524 A1    Dec. 8, 2005

Related U.S. Application Data

(60) Provisional application No. 60/558,873, filed on Apr. 2, 2004.

(51) Int. Cl.
*G01J 3/28* (2006.01)

(52) U.S. Cl. .................... 356/326; 356/328
(58) Field of Classification Search ............. 356/326, 356/328, 445, 333
See application file for complete search history.

(56) References Cited

U.S. PATENT DOCUMENTS

| | | | | |
|---|---|---|---|---|
| 4,856,897 A * | 8/1989 | Fateley et al. | ............... | 356/301 |
| 5,607,800 A | 3/1997 | Ziger | ............... | 430/8 |
| 5,631,735 A * | 5/1997 | Nagai | ............... | 356/330 |
| 5,739,909 A | 4/1998 | Blayo et al. | ............... | 356/369 |
| 5,867,276 A | 2/1999 | McNeil et al. | ............... | 356/445 |
| 5,889,593 A | 3/1999 | Bareket | ............... | 356/445 |
| 5,963,329 A | 10/1999 | Conrad et al. | ............... | 356/613 |
| 6,181,474 B1 * | 1/2001 | Ouderkirk et al. | ............... | 359/629 |
| 6,429,943 B1 | 8/2002 | Opsal et al. | ............... | 356/625 |
| 2002/0109841 A1 * | 8/2002 | Gould et al. | ............... | 356/318 |
| 2004/0065845 A1 * | 4/2004 | Seyfried | ............... | 250/458.1 |
| 2004/0145735 A1 * | 7/2004 | Silberberg et al. | ............... | 356/301 |
| 2005/0036202 A1 | 2/2005 | Cohen et al. | ............... | 359/495 |

FOREIGN PATENT DOCUMENTS

GB    2 191 855 A    12/1987

OTHER PUBLICATIONS

A.C. Akcay et al., "Spectral shaping to improve the point spread function in optical coherence tomography," *Optics Letters*, vol. 28, No. 20, Oct. 15, 2003, pp. 1921-1923.
W. Duncan et al., "DLP™ Switched Blaze Grating; the Heart of Optical Signal Processing," *MOEMS and Miniaturized Systems III, Proceedings of SPIE*, vol. 4983 (2003), pp. 297-304.

(Continued)

*Primary Examiner*—Gregory J. Toatley, Jr.
*Assistant Examiner*—Kara Giesel
(74) *Attorney, Agent, or Firm*—Stallman & Pollock LLP (57) ABSTRACT

An optical filter for the selective attenuation of specific wavelengths of light includes at least one spectrally dispersive element, such as a diffraction grating or prism, in combination with an optical filter. A dispersive element separates broadband light into a constituent wavelength spread in angle space. An optical filter, or filter array, can block and/or attenuate specific wavelengths or wavelength ranges of interest while the light is angularly dispersed. A second dispersive element can recombine this filtered, separated wavelength fan of light into a coaxial broadband beam having a smoother intensity profile than the unfiltered beam.

24 Claims, 4 Drawing Sheets

OTHER PUBLICATIONS

Brochure by Newport, "Model OSP-9500 λ Commander Programmable Spectral Source," 78-Photonics (2004), 2 pages in length.

Brochure by Newport, "Model OSP-9100 λ Commander Programmable Spectral Processor," Photonics and Fiber Optics (2004), 2 pages in length.

Brochure by Newport, "λ Commander™ OSP-9100/OSP-9500 Programmable Spectral Processor and Programmable Spectral Source (Applications Optical Coherence Tomography)," Oct. 2003, 6 pages in length.

W. Duncan et al., "CommsDesign—Improving DWDM Performance with Optical Signal Processing," printed from URL:http://www.commsdesign.com/showArticle.jhtml?articleID=16505850, printed Jul. 7, 2005, 13 pages in length.

\* cited by examiner

BROADBAND WAVELENGTH SELECTIVE FILTER

CLAIM OF PRIORITY

This application claims priority to U.S. Provisional Patent Application No. 60/558,873, entitled "BROADBAND WAVELENGTH SELECTIVE FILTER," filed Apr. 2, 2004, which is hereby incorporated herein by reference.

TECHNICAL FIELD OF THE INVENTION

This invention relates to the non-destructive evaluation of samples, such as semiconductor wafers.

BACKGROUND

As semiconductor geometries continue to shrink, manufacturers have increasingly turned to optical techniques to perform non-destructive inspection and analysis of semiconductor wafers. Techniques of this type, known generally as optical metrology techniques, operate by illuminating a sample with a probe beam, then detecting and analyzing the reflected radiation. Ellipsometry and reflectometry are two examples of commonly used optical metrology techniques. For the specific case of ellipsometry, changes in the polarization state of the probe beam are analyzed. Changes in intensity are analyzed for reflectometry, while scatterometry is used when the structural geometry of a sample creates diffraction (optical scattering) of the probe beam. Scatterometry systems analyze diffraction to deduce details of the structures that cause the diffraction to occur.

Various optical techniques have been used to perform optical scatterometry. These include broadband spectroscopy (such as is described in U.S. Pat. Nos. 5,607,800; 5,867,276 and 5,963,329), spectral ellipsometry (U.S. Pat. No. 5,739,909) single-wavelength optical scattering (U.S. Pat. No. 5,889,593), and spectral and single-wavelength beam profile reflectance and beam profile ellipsometry (U.S. Pat. No. 6,429,943). Each of the above-listed patents is hereby incorporated herein by reference. Scatterometry generally refers to optical response information in the form of diffraction orders produced by periodic structures (e.g., gratings on a wafer). In addition, any of these measurement technologies, e.g., single-wavelength laser BPR or BPE, can be employed to obtain critical dimension (CD) measurements on non-periodic structures, such as isolated lines or isolated vias and mesas.

Figure 1:
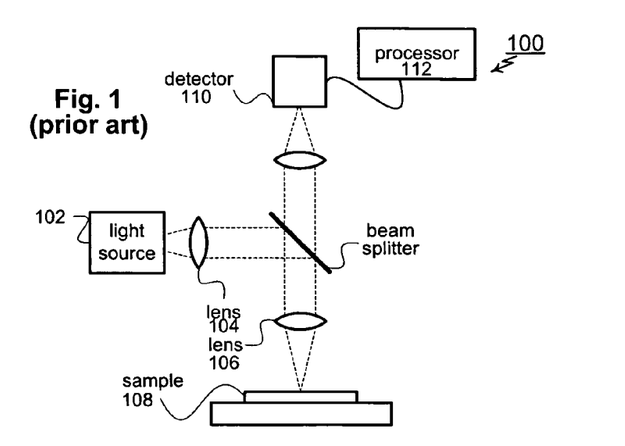
FIG. 1 is a block diagram of a prior art optical metrology tool.

FIG. 1 shows a diagram for a typical optical metrology tool, in which an illumination source 102 creates a monochromatic or polychromatic probe beam. The probe beam is projected by one or more lenses 104, 106 onto the surface of a sample 108. The sample reflects at least a portion of the probe beam, and the reflected portion is transported to a detector 110. The detector transforms the received energy into corresponding output signals. A processor 112 analyzes the signals to measure the structure or composition of the sample.

A polychromatic probe beam typically is used for broadband measurements. The spectral range of these probe beams can be quite large, such as from near-infrared to deep ultra-violet. Creating broadband probe beams is technically challenging. Typically, the outputs of two or more different sources must be combined to create the desired spectral range. The combined outputs then must be filtered to remove undesired components, such as infrared components, as well as to maximize constancy and minimize light contamination over the desired spectral range.

Optical filters exist in a broad array of configurations. There are filters that absorb or reflect various wavelength bands. These filters can be composed of bulk materials like colored glasses, or composed of dielectric stacks of thin films, for example, that combine to make a filter with the desired properties. It is extremely difficult, if not impossible, to manufacture filters that have specific desired attenuation properties from the deep ultra violet to the infrared because of material properties of bulk materials, such as glasses, and materials used for thin films. For example, there are sources that operate from the deep UV (e.g., 190-nm) to the near-infrared (e.g., 900-nm). Filters for these sources must have high transmissivity in that range and simultaneously block all longer wavelength light (e.g., above 950-nm) in order to prevent overheating of the optical system. While standard approaches for this problem exist, these approaches tend to be highly inefficient. In addition, when an optical spectrum is desired that has a smooth intensity, as a function of wavelength, and the spectral distribution contains a number of intensity spikes, such as in the case of Xenon arc lamps, it is virtually impossible to clean the spectrum with conventional filters without severely impacting the overall light throughput.

DETAILED DESCRIPTION

Systems and methods in accordance with various embodiments of the present invention overcome deficiencies in existing broadband optical devices by changing the way in which light is filtered. A number of optical filter systems and devices in accordance with embodiments of the present invention can be used for the selective attenuation and/or exclusion of specific wavelengths of light across a broadband spectrum.

Figure 2:
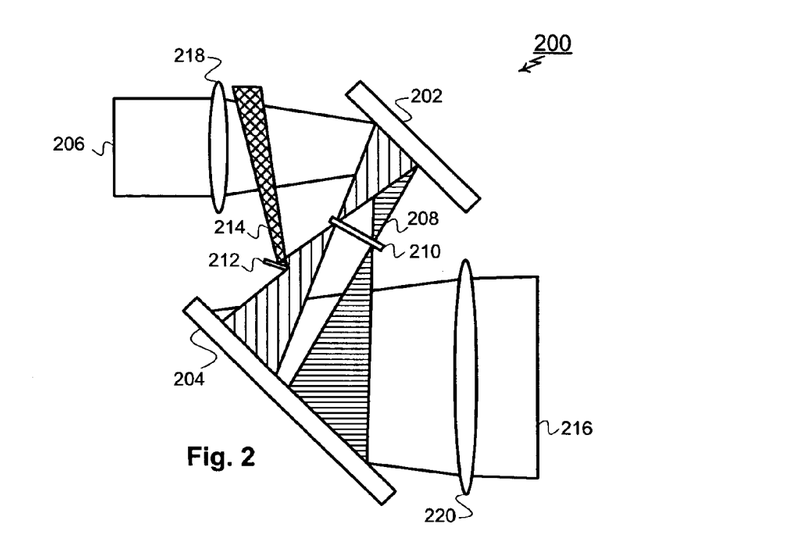
FIG. 2 shows an optical filter arrangement that can be used in accordance with one embodiment of the present invention.

FIG. 2 shows an arrangement for a filter system 200 that can be used in accordance with one embodiment of the present invention. The filter system includes a first grating 202 and a second grating 204, each of which can be any appropriate grating known in the art for broadband dispersion. A polychromatic beam of light 206 is focused by a lens element 218 onto the first grating 202, which disperses the beam into a ray fan 208 of constituent wavelengths. An optical filter 210 is positioned to receive the ray fan 208 as the fan comes to focus in a spectrum. The optical filter system 200 can include a long wavelength blocker 212 positioned to intercept the ray fan 208 and redirect (or alternately absorb) the long wavelength light rays 214. After filtering and (any) long wavelength blocking, the ray fan 208 is recombined by grating 204. The recombined light is collimated by lens 220, producing a filtered optical beam 216 in which selected spectral regions have been attenuated or eliminated.

Figure 3:
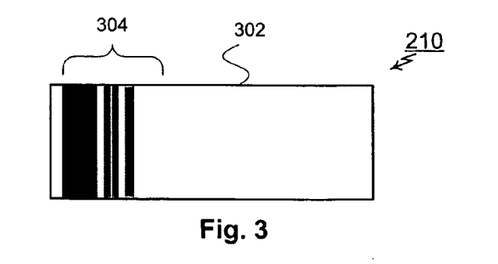
FIG. 3 shows a filter array that can be used with the optical filter arrangement of FIG. 2.

As shown in FIG. 3, the optical filter 210 can include a substrate 302 having a series of blocking and/or attenuation regions 304. Each of these regions 304 can be tailored to transmit a desired amount of light, as well as to absorb, reflect, scatter, and/or diffuse the remainder of the light.

Figure 4:
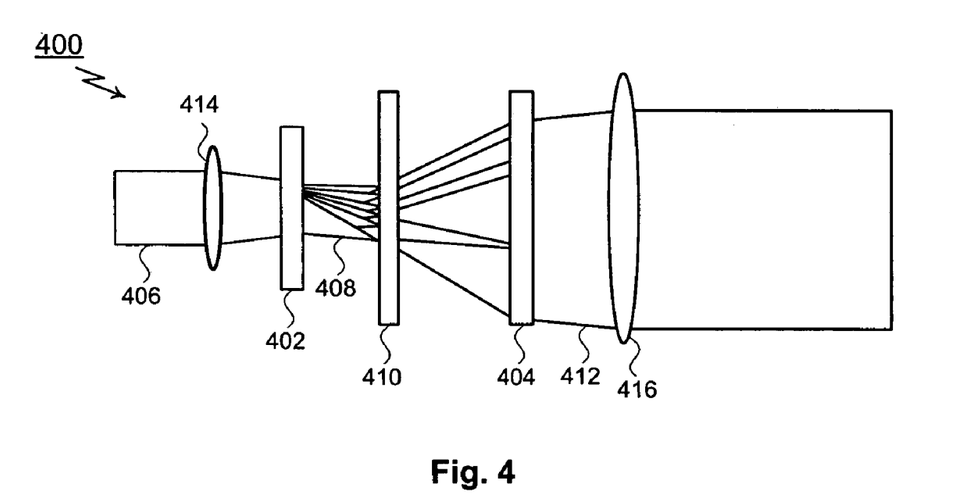
FIG. 4 shows an optical filter arrangement that can be used in accordance with another embodiment of the present invention.

FIG. 4 shows an optical filter system 400 in accordance with another embodiment of the present invention. Instead of using reflective gratings as in the system of FIG. 2, this optical filter includes transmission gratings 402 and 404. The transmission gratings can be any appropriate gratings known in the art for broadband dispersion. A polychromatic beam of light 406 can be passed through at least one focusing optical element, such as a focusing lens 414, and transmitted to the first transmissive grating 402. The first grating 402 can disperse the focused light into a ray fan 408 of constituent wavelengths. An optical filter 410 can be positioned near where the ray fan 408 comes to focus. The filter 410 can be similar or identical to the filter 210 described with respect to FIGS. 2 and 3. The optical filter arrangement 400 also can include long and/or short wavelength blockers (not shown) for absorbing and/or redirecting specific rays across the spectrum. After filtering, and any wavelength blocking, the ray fan 408 can be recombined by the second transmissive grating 404. The recombined beam can be collimated by at least one optical element, such as a collimating lens 416, to produce a filtered optical beam 412 in which selected spectral regions have been attenuated and/or eliminated.

Figure 5:
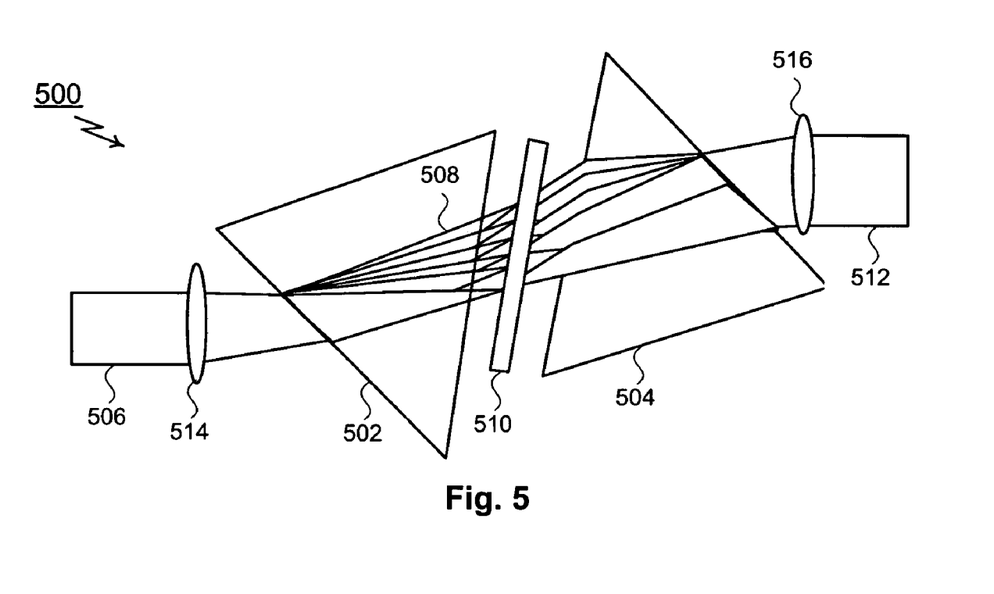
FIG. 5 shows an optical filter arrangement that can be used in accordance with another embodiment of the present invention.

FIG. 5 shows an optical filter system 500 in accordance with another embodiment of the present invention. In this arrangement, gratings such as those described with respect to FIGS. 2 and 4 can be replaced with dispersing prisms 502 and 504. These dispersing prisms can be any appropriate prisms known for use with broadband light. A polychromatic beam of light 506 is focused by an optical element, such as an appropriate focusing lens 514, and is dispersed by the first prism 502 into a ray fan 508 of constituent wavelengths. An optical filter 510 is positioned near a focus point of the ray fan 508. The optical filter 510 can be similar or identical to filter 210 described with respect to FIGS. 2 and 3. The optical filter 500 also can include long and/or short wavelength blockers (not shown), capable of absorbing and/or redirecting selected wavelengths of the ray fan. After filtering and any wavelength blocking, the ray fan 508 is recombined by a second prism 504 and collimated by at least one optical element, such as a collimating lens 516. A filtered optical beam 512 is produced, in which selected spectral regions have been attenuated and/or eliminated.

It should be noted that the arrangements described above are meant to be exemplary, and that any of a number of different arrangements and/or systems can be used to achieve similar results. For example, any of the above systems can include elements for blocking long or short wavelengths. Alternatively, any wave blocking can be done through the optical filter element. A system also can include more than one optical filter element. The filter elements in these systems can be reflective, transmissive, absorptive, or scattering, and the optical path of each system can be adjusted accordingly. Any lens can be replaced by an equivalent mirror or other appropriate optical element as known in the art. Lenses can be positioned on either side of the dispersive elements.

Figure 6:
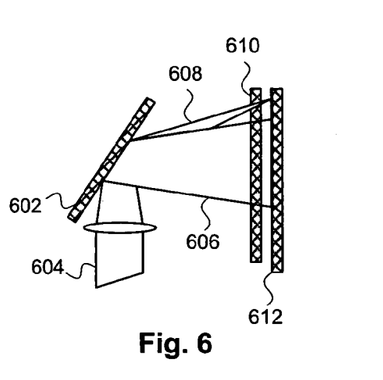
FIG. 6 shows an optical filter arrangement that can be used in accordance with another embodiment of the present invention.

Each of the filter arrangements described above is based on the spectral separation of an incoming beam into a ray fan, followed by optical filtering and recombination. These arrangements typically are used to shape spectrums near the light sources. In optical metrology tools, however, there are situations in which optical filtering needs to be done at or near the detector. In these instances, recombination may not be required. For such a situation, an optical filter arrangement 600 can be used such as is shown in FIG. 6. In this arrangement, a dispersive element 602, such as a reflective diffraction grating, receives a converging polychromatic light beam 604 from a focusing optical element. The dispersive element 602 diffracts the incident light into a wavelength dispersed ray fan 606, as well as a zero order, non-dispersed beam 608 that is typical of diffraction gratings. The ray fan and non-dispersed beam are incident on a filter array 610. The filter array 610 can be similar to the filter arrays described above, except that this filter array can be configured to selectively attenuate the zero order non-dispersed beam 608. This filter array also can be configured to smooth other spectral components. For this particular example, the filtered light then is incident on a detector or detector array 612.

Figure 7:
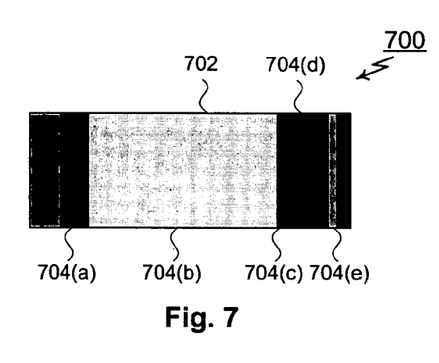
FIG. 7 shows a filter array that can be used with the optical filter system of FIG. 6.

FIG. 7 shows a filter array 700 that can be used with the arrangement of FIG. 6. This array includes a substrate 702 having a series of blocking and/or attenuation regions 704 (a)-(e). Each blocking/attenuating region can be tailored to transmit a desired amount of light, while absorbing, reflecting, or scattering diffuse non-desired light. This filter array 700 can be constructed using any appropriate technology, such as patterned dielectric or metallic coating technology. An exemplary filter array is formed of a broadband transmitting material, such as fused silica, with a blocking region 704(a) that eliminates the diffraction grating zero-order beam from interacting with the detector. This exemplary filter array also includes a tailored transmission dielectric filter stack coated region 704(b) for reducing the intensity of the visible portion of the spectrum by 50% and smoothing out the roughness of the curve. The filter array also includes a variety of attenuating dielectric filter stack coatings 704(c), 704(d), and 704(e), wherein each coating has a unique set of characteristics for altering the intensity of rays passing through that filter by a specified amount.

Figure 8:
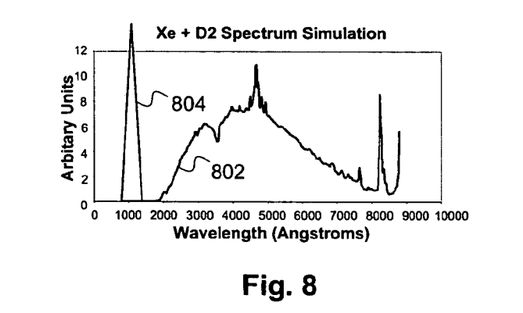
FIG. 8 is a graph showing optical intensity as a function of wavelength for an un-filtered probe beam.

FIG. 8 is a graph showing a representation of the energy received at the detector 612 in FIG. 6 as a function of wavelength. For this example, it is assumed that the filter array 610 is transparent and does not attenuate light at any wavelength. Two waveforms are shown, with the first waveform 802 corresponding to the wavelength dispersed ray fan 606 and the second waveform 804 corresponding to the zero order non-dispersed beam 608. As can be seen, the spectrum contains a number of spikes and is not very uniform.

Figure 9:
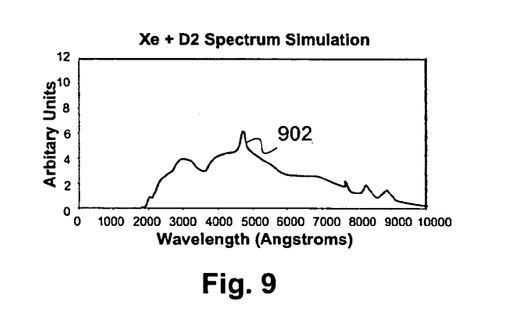
FIG. 9 is a graph showing optical intensity as a function of wavelength for a probe beam after processing by the optical filter arrangement of FIG. 6.

FIG. 9 is a graph showing another representation of the energy received at the detector as a function of wavelength, except that this plot assumes that the filter array 610 is configured as shown in FIG. 7. As discussed above, such an array is not completely transparent but instead attenuates the beam as a function of coating characteristics and position on the filter array. The effect is shown by waveform 902, where the zero order beam 608 has been removed and the waveforms across the spectral range of dispersed ray fan 606 have been attenuated. A significant difference can be seen for the infrared (IR) region, or the region above about 7500 Angstroms, where the presence of spikes has been greatly reduced relative to the plot of FIG. 8.

The filter arrays described above, including arrays 210, 410, 510 and 610, can be implemented using a range of different technologies. In one approach shown with respect to FIG. 10, a filter array 1000 can be formed as a substrate 1002 coated with a variable reflective neutral density filter coating. In this specific example, the coating includes a blocking region 1004(a), a clear region 1004(b), and specific spike attenuating segments 1004(c)-1004(e) that are selected to again remove large intensity fluctuations by wavelength. These regions can be formed in the variable coating by use of moving masks in the coating process or lithography techniques. The filter array alternatively can have a programmed attenuation coating, where the optical properties of the coating are actually programmed as a function of the linear position to correspond to, and compensate for, the actual fluctuations of the light source with wavelength. The stark discontinuities represented by segments 1004(c), 1004(d), and 1004(e) in the figure can be minimized or eliminated using such programming, whereby the coating reflectivity can smoothly track the inverse of the curve generated by the light source as a function of wavelength. Similar smoothing properties can be obtained using a laser writing technique on a photosensitive material, such as HEBS glass available from Canyon Materials of San Diego, Calif.

Figure 10:
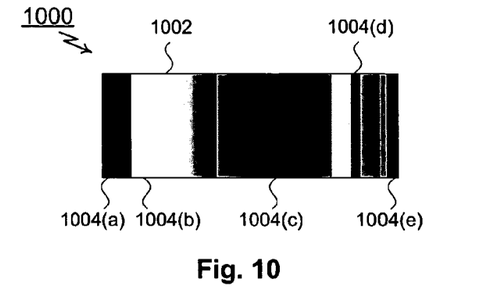
FIG. 10 shows a filter array that can be used with the optical filter arrangement of FIG. 6.
Figure 11:
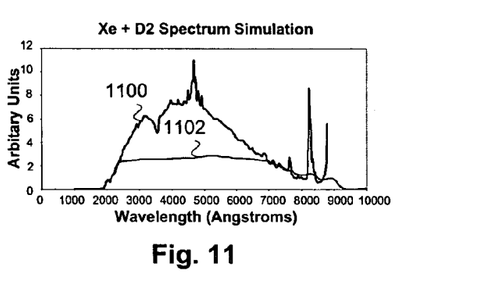
FIG. 11 is a graph showing optical intensity as a function of wavelength for a probe beam after processing by the optical filter of FIG. 6 and filter array of FIG. 10.

FIG. 11 is a graph showing energy received at the detector as a function of wavelength. Plot 1100 shows the energy received using a system such as the system of FIG. 6 without a variable filter. Plot 1102 shows the energy received when using a filter array as described with respect to FIG. 10. It can be seen that the filtered waveform 1102 is relatively flat and smooth when compared to the unfiltered waveform 1100. It should be noted that any zero order beam that would have been present in the unfiltered system would have been removed by the corresponding blocking region 1004(a) of the filter array.

Figure 12:
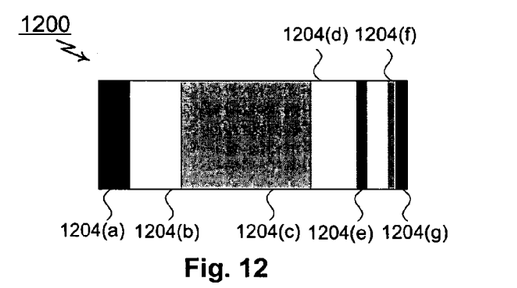
FIG. 12 shows a filter array that can be used with the optical filter arrangement of FIG. 6.

FIG. 12 shows a filter array 1200 that can be used in accordance with another embodiment of the present invention. This exemplary filter array 1200 can be assembled to include a number of regions. The array can be assembled by any appropriate means, such as by bonding together materials of appropriate thickness and optical transmissivity/reflectivity to form the desired filter array. For example, a dark glass (or metal) region 1204(a) can be used that is capable of blocking the zero order beam. A clear region 1204(b) can be included that is formed from a material such as fused silica or calcium fluoride, in order to transmit the UV portion of the spectrum. A visible attenuating filter glass region 1204(c), formed from a material such as Schott KG5, can be used to smooth or "bring down" a central peak. A section of fused silica 1204(d) or other appropriate material can allow the near-IR light to be un-attenuated. Specific segments of attenuating glasses 1204(e)-1204(g) can be used to minimize spikes over the IR region of the spectrum.

Figure 13:
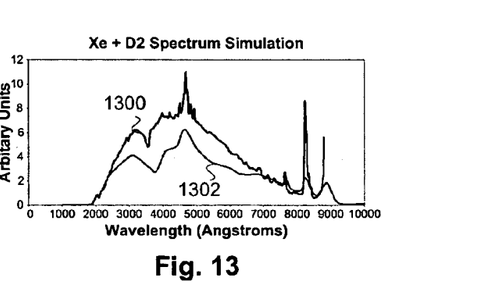
FIG. 13 is a graph showing optical intensity as a function of wavelength for a probe beam after processing by the optical filter of FIG. 6 and filter array of FIG. 12.

FIG. 13 is a graph showing energy received at the detector as a function of wavelength. Plot 1300 shows the energy received using a system such as the system of FIG. 6 without a variable filter. Plot 1302 shows the energy received when using a filter array as described with respect to FIG. 12. The filtered waveform 1302 is relatively flat and smooth when compared to the unfiltered waveform 1300. Any zero order beam is removed by the blocking region 1204(a) of the filter array. When forming the array, it can be desirable to first obtain plot 1300 in order to get a measure of the shape of the energy spectrum. An analysis then can be done on the curve, using parameters such as tolerance thresholds, local slope, or roughness values, in order to determine how the light would need to be filtered to produce a desired energy curve. A filter array then can be produced that contains a number of filter regions, having determined optical characteristics, necessary to bring the curve to within a desired shape range or smoothness. A balance can be met between the complexity of the filter and the shape of the curve, where necessary, in order to obtain acceptable results while keeping costs and complexity at a reasonable level.

Any of a number of other approaches can be used to create filter arrays similar to those described with respect to FIGS. 10 and 12. For example, filter arrays such as filter arrays 210, 410, 510 and 610 can be formed from photosensitive materials, such as laser written HEBS glass, as well as from liquid crystal material. Methods for forming and operating liquid crystal materials are known in the art and will not be discussed in detail herein.

As described above, the present invention provides a range of optical filters for the selective attenuation and/or exclusion of specific wavelengths of light from at least one broadband source. Each filter can use an initial optical element, such as a grating or prism, to spread an incoming beam of light into a ray fan. The incoming beam of light can include undesired spectral ranges (e.g., infrared radiation), and can lack the required degree of uniformity (e.g., includes too much illumination at one or more spectral ranges). The spread optical beam, or ray fan, can be passed through a filter array that can include transparent, translucent, and/or opaque regions. Specific spectral ranges can be eliminated by corresponding opaque regions, attenuated by corresponding translucent regions, or unaffected by corresponding transparent regions. Once filtered, the spread optical beam can be recombined by a second optical element, such as a grating or prism. The second optical element can be of a different type than the first optical element (e.g., a grating may be followed by a prism). Alternately, the second (re-combining) optical element optical element can be eliminated, such as where the filter is used as part of a spectrometer or other wavelength resolving detector. The filter array can be designed to act in reflection or in transmission, or in a combination of reflection and transmission.

It should be recognized that a number of variations of the above-identified embodiments will be obvious to one of ordinary skill in the art in view of the foregoing description. Accordingly, the invention is not to be limited by those specific embodiments and methods of the present invention shown and described herein. Rather, the scope of the invention is to be defined by the following claims and their equivalents.

What is claimed is:

1. An optical metrology tool for evaluating a sample, comprising:

a broadband light source for generating a polychromatic probe beam;

illuminating optics for directing the probe beam to illuminate a spot on the sample;

collection optics for collecting the probe beam light reflected from the sample;

a spectrometer for monitoring the intensity of the collected probe beam light as a function of wavelength and generating output signals in response thereto;

a processor for evaluating the sample based on the output signals; and a wavelength selective filter arrangement located in one of the illumination and collection paths prior to the spectrometer, said filter arrangement including;

a dispersive optical element to angularly disperse the probe beam as a function of wavelength; and a selective optical filter positioned to receive the angularly dispersed probe beam and selectively partially attenuate one or more wavelengths in the beam in order to partially reduce the intensity thereof so that the intensity of the spectrum received by the spectrometer is more uniform.

2. A tool according to claim 1, wherein:
the wavelength selective filter arrangement further includes a combining optical element positioned to receive the selectively attenuated probe beam and combine the probe beam into a filtered optical beam.

3. A tool according to claim 1, wherein:
the wavelength selective filter arrangement further includes a focusing optical element positioned to focus the probe beam onto the dispersive optical element.

4. A tool according to claim 1, wherein:
the dispersive optical element is selected from the group consisting of transmissive gratings, reflective gratings, and prisms.

5. A tool according to claim 1, further including:
a wavelength blocker positioned to intercept the angularly dispersed probe beam and operable to selectively remove a determined spectral range from the angularly dispersed probe beam.

6. A tool according to claim 1, wherein:
the selective optical filter includes a substrate having a series of attenuation regions, wherein each attenuation region is operable to transmit a specified amount of light for one or more wavelengths.

7. A tool according to claim 1, wherein said wavelength selective filter is further configured to shape the spectrum of the beam to selectively attenuate intensity spikes at selected wavelengths.

8. An optical metrology tool for evaluating a sample, comprising:
a broadband light source for generating a polychromatic probe beam;

illuminating optics for directing the probe beam to illuminate a spot on the sample;

collection optics for collecting the probe beam light reflected from the sample;

a spectrometer for monitoring the intensity of the collected probe beam light as a function of wavelength and generating output signals in response thereto;

a processor for evaluating the sample based on the output signals; and a wavelength selective filter arrangement located in one of the illumination and collection paths, said filter arrangement including;

a dispersive optical element to angularly disperse the probe beam as a function of wavelength; and a selective optical filter positioned to receive the angularly dispersed probe beam and selectively attenuate one or more wavelengths in the beam said filter arrangement for shaping the spectrum of the beam to selectively attenuate intensity spikes at selected wavelengths and wherein the wavelength selective filter arrangement further includes a focusing optical element positioned to focus the probe beam onto the dispersive optical element.

9. A tool according to claim 8, wherein: the wavelength selective filter arrangement is located prior to the spectrometer along the collection path.

10. A tool according to claim 8, wherein:
the wavelength selective filter arrangement further includes a combining optical element positioned to receive the selectively attenuated probe beam and combine the probe beam into a filtered optical beam.

11. A tool according to claim 8, wherein:
the dispersive optical element is selected from the group consisting of transmissive gratings, reflective gratings, and prisms.

12. A tool according to claim 8, further including:
a wavelength blocker positioned to intercept the angularly dispersed probe beam and operable to selectively remove a determined spectral range from the angularly dispersed probe beam.

13. A tool according to claim 8, wherein:
the selective optical filter includes a substrate having a series of attenuation regions, wherein each attenuation region is operable to transmit a specified amount of light for one or more wavelengths.

14. An optical metrology tool for evaluating a sample, comprising:
a broadband light source for generating a polychromatic probe beam;

illuminating optics for directing the probe beam to illuminate a spot on the sample;

collection optics for collecting the probe beam light reflected from the sample;

a spectrometer for monitoring the intensity of the collected probe beam light as a function of wavelength and generating output signals in response thereto;

a processor for evaluating the sample based on the output signals; and a wavelength selective filter arrangement located in one of the illumination and collection paths, said filter arrangement including;

a dispersive optical element to angularly disperse the probe beam as a function of wavelength;

a selective optical filter positioned to receive the angularly dispersed probe beam and selectively partially attenuate one or more wavelengths in the beam in order to partially reduce the intensity thereof so that the intensity of the spectrum received by the spectrometer is more uniform; and a combining optical element positioned to receive the selectively attenuated probe beam and combine the probe beam into a filtered optical beam.

15. A tool according to claim 14, wherein:
the wavelength selective filter arrangement is located prior to the spectrometer along the collection path.

16. A tool according to claim 14, wherein:
the wavelength selective filter arrangement further includes a focusing optical element positioned to focus the probe beam onto the dispersive optical element.

17. A tool according to claim 14, wherein:
the dispersive optical element is selected from the group consisting of transmissive gratings, reflective gratings, and prisms.

18. A tool according to claim 14, further including:
a wavelength blocker positioned to intercept the angularly dispersed probe beam and operable to selectively remove a determined spectral range from the angularly dispersed probe beam.

19. A tool according to claim 14, wherein:
the selective optical filter includes a substrate having a series of attenuation regions, wherein each attenuation region is operable to transmit a specified amount of light for one or more wavelengths.

20. A tool according to claim 14, wherein said wavelength selective filter is further configured to shape the spectrum of the beam to selectively attenuate intensity spikes at selected wavelengths.

21. An optical metrology tool for evaluating a sample, comprising:
a broadband light source for generating a polychromatic probe beam;
illuminating optics for directing the probe beam to illuminate a spot on the sample;
collection optics for collecting the probe beam light reflected from the sample;
a spectrometer for monitoring the intensity of the collected probe beam light as a function of wavelength and generating output signals in response thereto;
a processor for evaluating the sample based on the output signals; and
a wavelength selective filter arrangement located in one of the illumination and collection paths, said filter arrangement including;
a dispersive optical element to angularly disperse the probe beam as a function of wavelength;
a selective optical filter positioned to receive the angularly dispersed probe beam and selectively attenuate one or more wavelengths in the beam said filter arrangement for shaping the spectrum of the beam to selectively attenuate intensity spikes at selected wavelengths; and
a wavelength blocker positioned to intercept the angularly dispersed probe beam and operable to selectively remove a determined spectral range from the angularly dispersed probe beam.

22. A tool according to claim 21, wherein:
the wavelength selective filter arrangement further includes a focusing optical element positioned to focus the probe beam onto the dispersive optical element.

23. An optical metrology tool for evaluating a sample, comprising:
a broadband light source for generating a polychromatic probe beam;
illuminating optics for directing the probe beam to illuminate a spot on the sample;
collection optics for collecting the probe beam light reflected from the sample;
a spectrometer for monitoring the intensity of the collected probe beam light as a function of wavelength and generating output signals in response thereto;
a processor for evaluating the sample based on the output signals; and
a wavelength selective filter arrangement located in one of the illumination and collection paths, said filter arrangement including;
a dispersive optical element to angularly disperse the probe beam as a function of wavelength;
a selective optical filter positioned to receive the angularly dispersed probe beam and selectively attenuate one or more wavelengths in the beam;
a combining optical element positioned to receive the selectively attenuated probe beam and combine the probe beam into a filtered optical beam; and
a focusing optical element positioned to focus the probe beam onto the dispersive optical element.

24. An optical metrology tool for evaluating a sample, comprising:
a broadband light source for generating a polychromatic probe beam;
illuminating optics for directing the probe beam to illuminate a spot on the sample;
collection optics for collecting the probe beam light reflected from the sample;
a spectrometer for monitoring the intensity of the collected probe beam light as a function of wavelength and generating output signals in response thereto;
a processor for evaluating the sample based on the output signals; and
a wavelength selective filter arrangement located in one of the illumination and collection paths, said filter arrangement including;
a dispersive optical element to angularly disperse the probe beam as a function of wavelength;
a selective optical filter positioned to receive the angularly dispersed probe beam and selectively attenuate one or more wavelengths in the beam;
a combining optical element positioned to receive the selectively attenuated probe beam and combine the probe beam into a filtered optical beam; and
a wavelength blocker positioned to intercept the angularly dispersed probe beam and operable to selectively remove a determined spectral range from the angularly dispersed probe beam.

* * * * *